(12) United States Patent
Yaegashi et al.

(10) Patent No.: US 6,271,388 B1
(45) Date of Patent: Aug. 7, 2001

(54) PROCESS FOR PRODUCING OXAZOLIDIN-2-ONE DERIVATIVE

(75) Inventors: Keisuke Yaegashi; Yoshiro Furukawa; Hiroshi Yoshimoto, all of Amagasaki (JP)

(73) Assignee: Daiso Co., Ltd., Osaka-fu (JP)

( * ) Notice: Subject to any disclaimer, the term of this patent is extended or adjusted under 35 U.S.C. 154(b) by 0 days.

(21) Appl. No.: 09/623,757

(22) PCT Filed: Mar. 1, 1999

(86) PCT No.: PCT/JP99/00969

§ 371 Date: Sep. 8, 2000

§ 102(e) Date: Sep. 8, 2000

(87) PCT Pub. No.: WO99/46252

PCT Pub. Date: Sep. 16, 1999

(30) Foreign Application Priority Data

Mar. 10, 1998 (JP) .................................. 10-057860

(51) Int. Cl.$^7$ .................................. C07D 263/04
(52) U.S. Cl. .................................. 548/229
(58) Field of Search .................................. 548/229

(56) References Cited

U.S. PATENT DOCUMENTS

| 4,500,717 | 2/1985 | Cook et al. . |
| 4,521,626 | * 6/1985 | Kershner .................................. 564/487 |
| 5,969,146 | 10/1999 | Jegham et al. .................................. 548/232 |

OTHER PUBLICATIONS

Chem. Ber., 99, pp. 62–67 (1996) and Abstract thereof.
Chem. Ber., 99, pp. 55–61 (1996) and Abstract thereof.
Chem. Ber., 93, pp. 1975–1982 (1960) and Abstract thereof.

* cited by examiner

*Primary Examiner*—Deborah C. Lambkin
*Assistant Examiner*—Sonya N. Wright
(74) *Attorney, Agent, or Firm*—Wenderoth, Lind & Ponack, L.L.P.

(57) ABSTRACT

An industrial process for preparing an oxazolidin-2-one derivative represented by the following general formula (3)

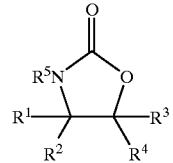

(3)

wherein $R^1$, $R^2$, $R^3$ and $R^4$ are hydrogen atom, straight, branched or cyclic alkyl group, straight or branched alkyl group substituted by alkoxy, substituted amino or alkylthio, substituted or unsubstituted aralkyl group, or substituted or unsubstituted aryl group, and $R^5$ is are hydrogen atom, straight, branched or cyclic alkyl group, substituted or unsubstituted aralkyl group, or substituted or unsubstituted aromatic ring,
which is characterized in reacting a 1,3-dioxolan-2-one derivative and a carbamate derivative or an urea derivative in the presence of a fluoride salt.

18 Claims, No Drawings

PROCESS FOR PRODUCING OXAZOLIDIN-2-ONE DERIVATIVE

This application is a 371 of PCT/JP99/00969 filed Mar. 1, 1999.

TECHNICAL FIELD

The present invention relates to a novel process for preparing an oxazolidin-2-one derivative useful for an intermediate for synthesis of medicines and agrochemicals.

BACKGRAUND ART

Oxazolidin-2-one derivatives are known from of old as industrially useful compounds. The compounds are especially useful in the medical field and many medicines prepared from the compounds have recently developed. Therefore, there are many kinds of reports on processes for preparation of the compounds. As an effective process among them is illustrated a process for preparation of the oxazolidin-2-one derivative from a 1,3-dioxolan-2-one derivative by ring-transformation.

This method is said to be an effective method, since a pre-material of a 1,3-dioxolan-2-one derivative, a starting material is prepared from a 1,2-diol derivative relatively easily available and the 1,3-oxazolidin-2-one derivative is prepared from the 1,2-diol derivative via a few steps.

Known and reported processes for preparing an oxazolidin-2-one derivative from a 1,3-dioxolan-2-one derivative by ring-transformation are illustrated as follows. (1) The method by reacting ethylene carbonate and a N,N'-diarylurea in the presence of lithium chloride (Chem. Ber., 99, 62 (1996)). (2) The method by reacting ethylene carbonate or propylene carbonate and an arylamine in the presence of lithium chloride (Chem. Ber., 99, 55 (1996)). (3) The method by reacting 4-methoxymethyl-1,3-dioxolan-2-one and a carbamate derivative in the presence of potassium carbonate (PCT Patent Publication A No. WO97/13768). (4) The method by reacting ethylene carbonate or propylene carbonate and an isocyanate derivative in the presence of lithium chloride (Chem. Ber., 93, 1975 (1960)).

DISCLOSURE OF INVENTION

However, the above known methods have following demerits in view of the industrial application of the methods.

Namely, the methods (1) to (3) need a 1,3-dioxolan-2-one derivative in amount of 1.8 moles or more than 1.8 moles for preparing an oxazolidin-2-one derivative in some degree of the yield and therefore, are not economical. In regard to the method (4), though its yield is good, an isocyanate derivative difficult for its synthesis and handling must be used as a starting material and the method is not suitable for mass production thereof. When an optically active 1,3-dioxolan-2-one derivative as a starting material in any above method is used, the optical purity significantly decreases due to occurrence of racemization during the reaction.

The present inventors have extensively studied and have found that an oxazolidin-2-one derivative represented by the following general formula (3) is easily prepared with good yield by reacting a 1,3-dioxolan-2-one derivative represented by the following general formula (1) and a carbamate derivative or an urea derivative represented by the following general formula (2) in the presence of a fluoride salt. Furthermore, when an optically active 1,3-dioxolan-2-one derivative (1) is used in this reaction, the oxazolidin-2-one derivative (3) is also prepared in optically active form.

Namely, the present invention relates to a process for preparing an oxazolidin-2-one derivative represented by the following general formula (3)

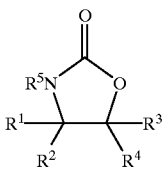

(3)

wherein $R^1$, $R^2$, $R^3$ and $R^4$ are hydrogen atom, straight, branched or cyclic alkyl group, straight or branched alkyl group substituted by alkoxy, substituted amino or alkylthio, substituted or unsubstituted aralkyl group, or substituted or unsubstituted aryl group, and $R^5$ is hydrogen atom, straight, branched or cyclic alkyl group, substituted or unsubstituted aralkyl group, or substituted or unsubstituted aromatic ring, which is characterized in reacting a 1,3-dioxolan-2-one derivative represented by the following general formula (1)

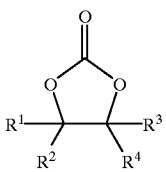

(1)

wherein $R^1$, $R^2$, $R^3$ and $R^4$ are the same as defined above, and a carbamate derivative or an urea derivative represented by the following general formula (2)

$R^5HNCOX$ (2)

wherein $R^5$ is the same as defined above, X is $OR^6$ or $NR^7R^8$ in which $R^6$ is lower alkyl, or substituted or unsubstituted aryl, and $R^7$ and $R^8$ are independently the same as $R^5$,
in the presence of a fluoride salt.

Examples of $R^1$, $R^2$, $R^3$ and $R^4$ in the general formula (1) are hydrogen, straight, branched or cyclic alkyl group, such as methyl, ethyl, isopropyl, cyclopropyl, or cyclohexyl, alkoxyalkyl group, such as methoxymethyl, methoxyethyl, or benzyloxymethyl, substituted aminoalkyl group, such as dimethylaminomethyl, piperidinoethyl, morpholinoethyl, N-benzyloxycarbonylpiperadinomethyl, N-methylpiperazinomethyl, or N-ethoxycarbonylmethyl-piperazinomethyl, alkylthioalkyl group, such as methylthiomethyl, or methylthioethyl, substituted or unsubstituted aralkyl group, such as benzyl, methylbenzyl, or methoxybenzyl, and substituted or unsubstituted aryl group, such as phenyl, tolyl, or methoxyphenyl. Preferable groups among them are hydrogen, $C_1$–$C_4$ lower alkyl group, methoxymethyl, benzyloxymethyl and benzyl.

Examples of $R^5$ in the general formula (2) are hydrogen, straight, branched or cyclic alkyl group, such as methyl, ethyl, isopropyl, or cyclopropyl, substituted or unsubstituted aralkyl group, such as benzyl, methybenzyl, or methoxybenzyl, substituted or unsubstituted aryl group, such as phenyl, cyanophenyl, tolyl, or methoxyphenyl, aromatic polycyclic ring, such as naphthalene or anthracene, or aromatic heterocyclic ring, such as furyl, thienyl, pyridyl, pyrimidinyl, quinolyl, benzofuryl, or benzothienyl. Preferable groups among them are hydrogen, $C_1$–$C_4$ lower alkyl group, benzyl, phenyl, cyanophenyl, naphthyl, or thienyl.

Examples of $R^6$ in the general formula (2) are lower alkyl group, such as methyl, ethyl, or t-butyl, or substituted or unsubstituted aryl group, such as phenyl, methoxyphenyl, or nitrophenyl. Examples of $R^6$ or $R^7$ are the same as examples of $R^5$. Preferable examples of them are $C_1$–$C_4$ lower alkyl and phenyl.

The amount of the carbamate derivative or the urea derivative (2) is 0.5 mole or more than 0.5 mole to 1,3-dioxolan-2-one derivative (1), preferably 0.8 to 1.5 moles, further preferably 0.9 to 1.1 moles.

The fluoride salts are preferably quaternary ammonium fluorides, alkali metal fluorides, or alkaline earth metal fluorides, especially preferably alkali metal fluorides or alkaline earth metal fluorides. These salts may be used alone or in combination of them and may be used in form being supported on an appropriate carrier.

Examples of the quaternary ammonium fluorides are tetramethylammonium fluoride, tetraethylammonium fluoride, tetrabutylammonium fluoride, tetraoctylammonium fluoride, and benzyltrimethylammonium fluoride.

Examples of the alkali metal fluorides are sodium fluoride, potassium fluoride, and cesium fluoride. Examples of the alkaline earth metal fluorides are magnesium fluoride and calcium fluoride. Examples of the carrier are zeolite, alumina, silica gel, molecular sieves, modified material thereof and so on.

The amount of the fluoride salt is preferably 0.001 to 10 moles to the substrate, a 1,3-dioxolan-2-one derivative, especially preferably 0.01 to 1 mole. To use it less than 0.001 mole makes the reaction very slow. On the other hand, to use it in excess of 10 moles does not give bad effect the reaction, but it is not economical. Depending on the solvent, the excess of the salt becomes insoluble and to stir the reaction mixture becomes difficult.

The solvents are aprotic solvents, such as N,N-dimethylformamide or dimethyl sulfoxide, ethers, such as diglyme, triglyme, 1,4-dioxane, 1,2-dimethoxyethane, or t-butylmethyl ether, chlorinated solvents such as chloroform or dichloroethane, or a mixture thereof, preferably N,N-dimethylformamide or dimethyl sulfoxide.

The reaction temperature is from 50° C. under heating to reflux temperature of the solvent, preferably from 100° C. to 150° C.

After finishing the reaction, insoluble materials such as a metal fluoride are removed by filtration, excess solvent is distilled off in vacuo, and the residue is purified by distillation, recrystallization and subjecting to chromatography to give easily the object oxazolidin-2-one derivative (3).

When an optically active 1,3-dioxolan-2-one derivative (1) is used as a starting material, an optically active oxazolidin-2-one derivative (3) is prepared without any significant racemization reaction during the reaction.

BEST MODE FOR CARRYING OUT THE INVENTION

The present invention is explained in the following examples, but the present invention should not be limited by the examples. Comparative examples 1 and 2 are examples prepared by using other bases than fluoride salts

EXAMPLE 1

Process for Preparing Oxazolidin-2-one:

Urea (34.1 g, 0.568 mmol) was dissolved in dimethyl sulfoxide (200 ml), and thereto were added cesium fluoride (8.63 g, 56.8 mmol) and 1,3-dioxolan-2-one (50.0 g, 0.568 mol), in order. The mixture was stirred for 24 hours at 140° C. under an atmosphere of argon. After filtering off the insoluble materials, the filtrate was condensed in vacuo, and the residue was purified by distillation to give the subject oxazolidin-2-one (33.4 g, yield 66.8%).

EXAMPLE 2

Process for Preparing (R)-5-methoxymethyloxazolidin-2-one:

Urea (246 g, 4.09 mmol) was dissolved in dimethyl sulfoxide (2.27 L), and thereto were added cerium fluoride (69.0 g, 0.454 mol) and (S)-4-methoxymethyl-1,3-dioxolan-2-one (600 g, 4.54 mol, optical purity 98.9%ee), in order. The mixture was stirred for 36 hours at 140° C. under an atmosphere of argon. After filtering off the insoluble materials, the filtrate was condensed in vacuo, and the residue was purified by distillation to give the subject (R)-5-methoxymethyloxazolidin-2-one (445 g, yield 74.7%, optical purity 98.6%ee).

EXAMPLE 3

Process for Preparing 5-methoxymethyloxazolidin-2-one:

Urethane (82.4 g, 0.925 mol) was dissolved in dimethyl sulfoxide (400 mL), and thereto were added potassium fluoride (48.8 g, 0.841 mol) and 4-methoxymethyl-1,3-dioxolan-2-one (111 g, 0.841 mol), in order. The mixture was stirred for 77 hours at 140° C. under an atmosphere of argon. After filtering off the insoluble materials, the filtrate was condensed in vacuo, and the residue was purified by distillation to give the subject 5-methoxymethyloxazolidin-2-one (76.0 g, yield 68.9%).

EXAMPLE 4

Process for Preparing (R)-5-methoxymethyloxazolidin-2-one:

Urethane (37.4 g, 0.420 mmol) was dissolved in N,N-dimethylformamide (200 mL), and thereto were added cesium fluoride (5.80 g, 38.2 mmol) and (S)-4-methoxymethyl-1,3-dioxolan-2-one (50 g, 0.382 mol, optical purity 97.7%ee), in order. The mixture was stirred for 72 hours at 140° C. under an atmosphere of argon. After filtering off the insoluble materials, the filtrate was condensed in vacuo, and the residue was purified by distillation to give the subject (R)-5-methoxymethyloxazolidin-2-one (35.1 g, yield 69.6 %, optical purity 97.3%ee).

EXAMPLE 5

Process for Preparing 3-phenyl-5-methoxymethyloxazolidin-2-one:

Phenylurethane (15.0 g, 90.9 mmol) was dissolved in N,N-dimethylformamide (40 mL), and thereto were added cesium fluoride (1.15 g, 7.57 mmol) and 4-methoxymethyl-1,3-dioxolan-2-one (10.0 g, 75.7 mol), in order. The mixture was stirred for 50 hours at 140° C. under an atmosphere of argon. After filtering off the insoluble materials, the filtrate was condensed in vacuo, and the residue was purified by silica gel chromatography to give the subject 3-phenyl-5-methoxymethyloxazolidin-2-one (12.8 g, yield 81.6%).

EXAMPLE 6

Process for Preparing 3-(2-naphthyl)-5-methoxymethyloxazolidin-2-one:

2-Naphthylurethane (19.3 g, 90.9 mmol) was dissolved in dimethyl sulfoxide (40 mL), and thereto were added cesium fluoride (1.15 g, 7.57 mmol) and 4-methoxymethyl-1,3- dioxolan-2-one (10.0 g, 75.7 mol), in order. The mixture was stirred for 32 hours at 140° C. under an atmosphere of argon. After filtering off the insoluble materials, the filtrate was condensed in vacuo, and the residue was purified by silica gel chromatography to give the subject 3-(2-naphthyl-5-methoxymethyloxazolidin-2-one (15.2 g, yield 78.1%).

EXAMPLE 7

Process for preparing (S)-5-methyloxazolidin-2-one:

Urea (29.4 g, 0.490 mol) was dissolved in dimethyl sulfoxide (200 mL), and thereto were added cesium fluoride (7.44 g, 49.0 mmol) and (S)-4-methyl-1,3-dioxolan-2-one (50.0 g, 0.490 mol, optical purity 98.7%ee), in order. The mixture was stirred for 30 hours at 140° C. under an atmosphere of argon. After filtering off the insoluble materials, the filtrate was condensed in vacuo, and the residue was purified by distillation to give the subject (S)-5-methyloxazolidin-2-one (33.4 g, yield 66.8%, optical purity 98.5%ee).

EXAMPLE 8

Process for Preparing 3-phenyl-5-methyloxazolidin-2-one:

N,N'-Diphenylurea (20.7 g, 98.0 mmol) was dissolved in dimethyl sulfoxide (40 mL), and thereto were added cesium fluoride (1.48 g, 9.80 mmol) and 4-methyl-1,3-dioxolan-2-one (10.0 g, 98.0 mmol), in order. The mixture was stirred for 30 hours at 140° C. under an atmosphere of argon. After filtering off the insoluble materials, the filtrate was condensed in vacuo, and the residue was recrystallized from ethanol to give the subject 3-phenyl-5-methyloxazolidin-2-one (12.9 g, yield 74.3%).

EXAMPLE 9

Process for Preparing (R)-3-benzyl-5-methoxymethyloxazolidin-2-one:

Benzylurethane (15.0 g, 83.9 mmol) was dissolved in dimethyl sulfoxide (40 mL), and thereto were added cesium fluoride (1.16 g, 7.63 mmol) and (S)-4-methoxymethyl-1,3-dioxolan-2-one (10.0 g, 76.3 mmol, optical purity 98.4%ee), in order. The mixture was stirred for 28 hours at 140° C. under an atmosphere of argon. After filtering off the insoluble materials, the filtrate was condensed in vacuo, and the residue was purified by silica gel chromatography to give the subject (R)-3-benzyl-5-methoxymethyloxazolidin-2-one (14.1 g, yield 83.5%, optical purity 98.2%ee).

Comparative Example 1

Process for Preparing 5-methoxymethyloxazolidin-2-one:

Urethane (10.0 g, 113 mmol) was dissolved in N,N-dimethylformamide (40 ml), and thereto were added potassium carbonate (20.8 g, 151 mmol) and 4-methoxymethyl-1,3-dioxolan-2-one (10.0 g, 75.7 mmol), in order. The mixture was stirred for 100 hours at 140° C. under an atmosphere of argon. After filtering off the insoluble materials, the filtrate was condensed in vacuo, and the residue was purified by silica gel chromatography give the subject 5-methoxymethyloxazolidin-2-one (2.3g, yield 23.1%).

Comparative Example 2

Process for Preparing 5-methoxymethyloxazolidin-2-one:

Urethane (10.0 g, 113 mmol) was dissolved in N,N-dimethylformamide (40 ml), and thereto were added sodium methoxide (409 mg, 7.57 mmol) and 4-methoxymethyl-1,3-dioxolan-2-one (10.0 g, 75.7 mmol), in order. The mixture was stirred for 80 hours at 140° C. under an atmosphere of argon. After filtering off the insoluble materials, the filtrate was condensed in vacuo, and the residue was purified by silica gel chromatography to give the subject 5-methoxymethyloxazolidin-2-one (4.3 g, yield 43.3%).

What is claimed is:

1. A process for preparing an oxazolidin-2-one derivative represented by the following general formula (3):

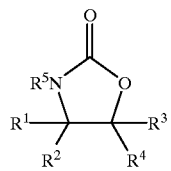

(3)

wherein $R^1$, $R^2$, $R^3$ and $R^4$ are hydrogen atom, straight, branched or cyclic alkyl group, straight or branched alkyl group substituted by alkoxy, substituted amino or alkylthio, substituted or unsubstituted aralkyl group, or substituted or unsubstituted aryl group, and $R^5$ is hydrogen atom, straight, branched or cyclic alkyl group, substituted or unsubstituted aralkyl group, or substituted or unsubstituted aromatic ring, which comprises reacting a 1,3-dioxolan-2-one derivative represented by the following general formula (1):

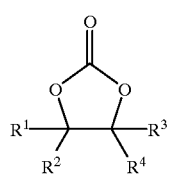

(1)

wherein $R^1$, $R^2$, $R^3$ and $R^4$ are the same as defined above, and a carbamate derivative or an urea derivative represented by the following formula (2):

$R^5HNCOX$ (2)

wherein $R^5$ is the same as defined above, X is $OR^6$ or $NR^7R^8$ in which $R^6$ is lower alkyl, or substituted or unsubstituted aryl, and $R^7$ and $R^8$ are independently the same as $R^5$, in the presence of a fluoride salt in a solvent of N,N-dimethylformamide or dimethyl sulfoxide.

2. A process for preparing an oxazolidin-2-one derivative represented by the following general formula (3a):

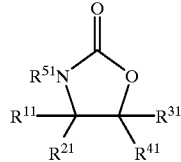

(3a)

wherein $R^{11}$, $R^{21}$, $R^{31}$ and $R^{41}$ are hydrogen atom, $C_1$–$C_4$ lower alkyl group, methoxymethyl group, benzyloxymethyl group or benzyl group and $R^{51}$ is hydrogen atom, $C_1$–$C_4$ lower alkyl group, benzyl group, phenyl group, cyanophenyl group, naphthyl group or thienyl group, which comprises reacting a 1,3-dioxolan-2-one derivative represented by the following general formula (1a):

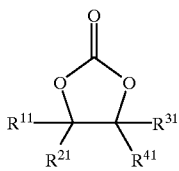
(1a)

wherein $R^{11}$, $R^{21}$, $R^{31}$ and $R^{41}$ are the same as defined above, and a carbamate derivative or an urea derivative represented by the following general formula (2a):

$$R^5HNCOX^1 \qquad (2a)$$

wherein $R^{51}$ is the same as defined above, $X^1$ is $OR^{61}$ or $NR^{71}R^{81}$ in which $R^{61}$ is $C_1$–$C_4$ lower alkyl group or phenyl group, $R^{71}$ and $R^{81}$ are the same as $R^{51}$, in the present of a fluoride salt in a solvent of N,N-dimethylformamide or dimethyl sulfoxide.

3. The process for preparing the oxazolidin-2-one derivative of claim 1, wherein the fluoride salt is an alkali metal fluoride or an alkaline earth metal fluoride.

4. The process for preparing the oxazolidin-2-one derivative of claim 2, wherein the fluoride salt is an alkali metal fluoride or an alkaline earth metal fluoride.

5. The process for preparing the oxazolidin-2-one derivative of claim 1, wherein the fluoride salt is cesium fluoride or potassium fluoride.

6. The process for preparing the oxazolidin-2-one derivative of claim 1, wherein the fluoride salt is cesium fluoride or potassium fluoride.

7. The process for preparing the oxazolidin-2-one derivative of claim 3, wherein the fluoride salt is cesium fluoride or potassium fluoride.

8. The process for preparing the oxazolidin-2-one derivative of claim 4, wherein the fluoride salt is cesium fluoride or potassium fluoride.

9. The process for preparing the oxazolidin-2-one derivative of claim 1, which comprises preparing an optically active oxazolidin-2-one derivative (3) by using an optically active 1,3-oxazolidin-2-one derivative (1) as a starting material.

10. The process for preparing the oxazolidin-2-one derivative of claim 2, which comprises preparing an optically active oxazolidin-2-one derivative (3a) by using an optically active 1,3-oxazolidin-2-one derivative (1a) as a starting material.

11. The process for preparing the oxazolidin-2-one derivative of claim 3, which comprises preparing an optically active oxazolidin-2-one derivative (3) by using an optically active 1,3-oxazolidin-2-one derivative (1) as a starting material.

12. The process for preparing the oxazolidin-2-one derivative of claim 4, which comprises preparing an optically active oxazolidin-2-one derivative (3a) by using an optically active 1,3-oxazolidin-2-one derivative (1a) as a starting material.

13. The process for preparing the oxazolidin-2-one derivative of claim 5, which comprises preparing an optically active oxazolidin-2-one derivative (3) by using an optically active 1,3-oxazolidin-2-one derivative (1) as a starting material.

14. The process for preparing the oxazolidin-2-one derivative of claim 6, which comprises preparing an optically active oxazolidin-2-one derivative (3a) by using an optically active 1,3-oxazolidin-2-one derivative (1a) as a starting material.

15. The process for preparing the oxazolidin-2-one derivative of claim 7, which comprises preparing an optically active oxazolidin-2-one derivative (3) by using an optically active 1,3-oxazolidin-2-one derivative (1) as a starting material.

16. The process for preparing the oxazolidin-2-one derivative of claim 8, which comprises preparing an optically active oxazolidin-2-one derivative (3a) by using an optically active 1,3-oxazolidin-2-one derivative (1a) as a starting material.

17. A process for preparing an oxazolidin-2-one derivative represented by the following general formula (3):

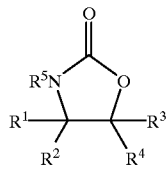
(3)

wherein $R^1$, $R^2$, $R^3$ and $R^4$ are hydrogen atom, straight, branched or cyclic alkyl group, straight or branched alkyl group substituted by alkoxy, substituted amino or alkylthio, substituted or unsubstituted aralkyl group, or substituted or unsubstituted aryl group, and $R^5$ is hydrogen atom, straight, branched or cyclic alkyl group, substituted or unsubstituted aralkyl group, or substituted or unsubstituted aromatic ring, which comprises reacting a 1,3-dioxolan-2-one derivative represented by the following general formula (1):

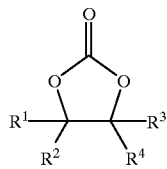
(1)

wherein $R^1$, $R^2$, $R^3$ and $R^4$ are the same as defined above, and a carbamate derivative or an urea derivative represented by the following formula (2):

$$R^5HNCOX \qquad (2)$$

wherein $R^5$ is the same as defined above, X is $OR^6$ or $NR^7R^8$ in which $R^6$ is lower alkyl, or substituted or unsubstituted aryl, and $R^7$ and $R^8$ are independently the same as $R^5$, in the presence of an alkyl metal fluoride or an alkaline earth metal fluoride.

18. The process for preparing the oxazolidin-2-one derivative of claim 17, wherein the alkali metal fluoride is cesium fluoride or potassium fluoride.

* * * * *